United States Patent [19]

Hodson et al.

[11] 4,094,968

[45] June 13, 1978

[54] TREATMENT FOR ALLERGY AND METHOD OF COMPOSITION THEREOF

[75] Inventors: Harold Francis Hodson, Hayes; John Frederick Batchelor, Beckenham, both of England

[73] Assignee: Burroughs Wellcome Co., Research Triangle Park, N.C.

[21] Appl. No.: 635,768

[22] Filed: Nov. 26, 1975

Related U.S. Application Data

[62] Division of Ser. No. 394,423, Sep. 5, 1973, Pat. No. 3,939,173.

[51] Int. Cl.$^2$ .................. A61K 9/14; A61L 9/04; A61K 31/41

[52] U.S. Cl. ........................................ 424/46; 424/45; 424/269

[58] Field of Search ............................ 424/45, 46, 269

[56] References Cited

U.S. PATENT DOCUMENTS 3,706,768   12/1972   Bays .................................. 424/269 X Primary Examiner—Frederick E. Waddell
Attorney, Agent, or Firm—Donald Brown

[57] ABSTRACT

Fluorenone and anthraquinone compounds substituted by at least one tetrazolyl group in one ring, and further substituted in the other ring, optionally for the fluorenones, have antiallergic activity.

30 Claims, No Drawings

TREATMENT FOR ALLERGY AND METHOD OF COMPOSITION THEREOF

This is a division of application Ser. No. 394,423, filed on Sept. 5, 1973 now U.S. Pat. No. 3,939,173.

The invention relates to tricyclic compounds having medicinal properties, the synthesis of the compounds and their adaptation for medicinal use.

It has been found that tricyclic compounds of formula I defined hereinbelow are active in mammals and in in vitro mammalian preparations as inhibitors of allergic reactions associated with reaginic antibodies of the kind responsible for asthma in man, and that this effect is attributable to the suppression of the release of anaphylactic mediators.

In formula I

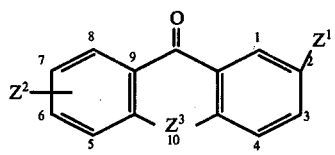

at least one of $Z^1$ and $Z^2$ is a 5-(1-R)tetrazolyl or a 5-(2-R)tetrazolyl group wherein R is hydrogen or alkyl having 1 to 6 carbon atoms, and the other is selected from carboxy, 5-(1-R)tetrazolyl and 5-(2-R)tetrazolyl as defined;

$Z^3$ represents a bond or is carbonyl; and when $Z^3$ represents a bond, $Z^2$ is also selected from hydrogen, nitro, cyano, halogen preferably chlorine or bromine, alkylsulphinyl, alkylsulphonyl, acyl, alkyl or alkoxy wherein the "alkyl" moiety of each of the acyl, alkyl, alkoxy, alkylsulphinyl, and alkylsulphonyl groups has 1 to 6 carbon atoms;

together with salts, and where one of $Z^1$ or $Z^2$ is carboxyl, amides and esters of said compounds.

Compounds of formula I include 2-$Z^1$, 7-$Z^2$-fluorenones, and 2-$Z^1$,6-$Z^2$-anthraquinones in which compounds at least one of $Z^1$ and $Z^2$ is 5-tetrazolyl and the other is selected from 5-tetrazolyl and carboxy, together with salts of said compounds.

Esters of compounds of formula I include alkyl esters having 1 to 6 carbon atoms, and amides include N-alkyl- and N,N-dialkylamides wherein the alkyl groups have 1 to 6 carbon atoms.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of peritoneal mast cells from actively sensitised rats (see for example, 1. Acta Pharmacol. et Toxicol. 30, supp. 1 (1971), 2. Thorax, 27/1, 38 (1972), and (c), by measurement of the histamine released from human chopped lung tissue passively sensitised in vitro with reaginic antibody when challenged with the homologous antigen (Br. Med. J. 3,272 (1968)). The activity of acids of formula I has been demostrated as described hereinabove using solutions of the carboxylate anion.

For the sake of convenience, compounds of formula I wherein either of $Z^1$ and $Z^2$ is an alkyl carboxylate group, shall hereinafter be referred to as 'esters' of formula I. Similarly references to 'amides' of formula I shall be construed as references to compounds of formula I wherein one of $Z^1$ and $Z^2$ is an optionally substituted carboxamide, and references to 'salts' of formula I shall means compounds of formula I wherein one or both of $Z^1$ and $Z^2$ is a carboxylate or tetrazolyl salt group.

Pharmaceutically acceptable salts of formula I include ammonium salts, alkali metal salts such as sodium and potassium salts, alkaline earth salts such as magnesium and calcium salts, and salts of organic bases, for example, amine salts such as triethanolamine and diethylaminoethylamine salts, and piperazine and morpholine salts. Especially valuable are water soluble salts of formula I most preferably those having a solubility in water of at least 1 mg/ml.

The anti-allergic activity of the salts of formula I lies in the anion and the nature of the cation does not contribute to the activity, but for medicinal purposes the cation must of course be pharmaceutically acceptable.

Pharmaceutically acceptable cations in compounds of formula I include hydrogen, ammonium, alkali metal cations such as sodium and potassium, alkaline earth metal cations such as calcium and magnesium and organic base cations, for example, alkylammonium cations of such alkylamines as triethanolamine and diethylaminoethylamine, piperazinium and morpholinium cations.

Suitable substituted carboxamide groups include N-alkyl and N,N-dialkyl substituted carboxamide groups wherein the alkyl moiety is an alkyl group having 1 to 6 carbon atoms, preferably 1 to 4 carbon atoms.

Preparation of compounds of formula I may be effected by any method known in the art of preparing them and compounds of analogous chemical structure. In general the compounds of formula I wherein one of $Z^1$ and $Z^2$ is a carboxylate derivative (for example an amide, ester or salt), are prepared by suitable treatment of the corresponding acid. However, in certain circumstances it is possible to prepare such derivatives without prior isolation of the carboxylic acid, either by the choice of suitable reactants or by forming the desired derivative in a reaction mixture of the acid, without first isolating the acid.

Methods for the preparation of compounds and salts of formula I are described hereinbelow, but it will be understood that in some instances the methods maybe adopted to yield the corresponding esters or amides of formula I 1. Hydrolysis of a compound of formula II

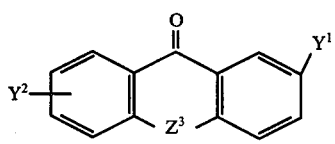

wherein one of $Y^1$ and $Y^2$ is a carboxyl group precursor, such as a nitrile group, trichloromethyl group or a group $COL^1$ wherein $L^1$ is a leaving group, such as a nucleophilic atom or group, for example, a trichloromethyl group, an optionally substituted amino group, a halogen atom or an alkoxy group; and the other of $Y^1$ and $Y^2$ is the group $Z^1$ or $Z^2$, as appropriate, as defined in formula I; and $Z^3$ has the meaning defined in formula I. Hydrolysis is conveniently effected by heating a compound of formula II with a dilute aqueous alkali, or with a dilute aqueous mineral acid optionally with an organic acid. For example, one may use dilute sulphuric acid, dilute hydrochloric acid with acetic acid, or dilute aqueous sodium hydroxide solution. Hydrolysis with aqueous alkali will yield inter alia an aqueous solution of a dicarboxylate salt but if it is desired to collect the maximum amount of carboxylic acid, then the reaction mixture should be acidified when hydrolysis is completed to precipitate the acid. On the other hand if the desired end-product is the carboxylate salt, then following hydrolysis, the cation of the desired salt may be added to precipitate the desired salt by the common ion effect without prior isolation of the corresponding acid.

By means of nucleophilic substitution reactions analogous to hydrolysis, for example, alcoholysis and ammonolysis, compounds of formula I other than the carboxylic acid may be prepared directly from compounds of formula II. Thus reaction of a compound of formula II with an appropriate alcohol yields an ester of formula I, and reaction with ammonia or an appropriate primary or secondary amine yields an amide of formula I.

2. Cyclisation of a compound of formula III

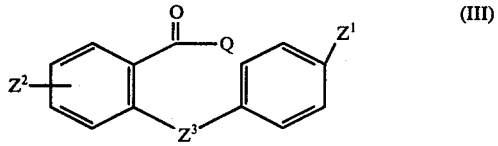
(III)

wherein $Z^1$, $Z^2$ and $Z^3$ have the meaning defined in formula I and Q is a hydroxyl, alkoxy or an optionally substituted amino group, a halogen atom, or a $RCO_2$ group, a $ROCO_2$ group or a $RSO_3$ group wherein R is alkyl or aryl. Cyclisation may be affected by heating a compound of formula III at an elevated temperature, for example up to about 300° C. Preferably heating is carried out in the presence of a Lewis acid under anhydrous conditions or a protonic acid, optionally in the presence of a non-polar solvent. Preferred Lewis acids include boron trifluoride and aluminium trichloride and preferred protonic acids include sulphuric, hydrochloric and polyphosphoric acids. If, however, $Z^2$ is a carboxylate substituent in the 5-position of the nascent compound of formula I, reaction conditions and/or the group Q must be chosen so as to avoid reaction of the group $Z^2$.

In the case of anthoraquinone compounds of formula I cyclisation to form the carbonyl linkage in the tricyclic nucleus may be effected to form either of the two carbonyl linkages of the tricyclic anthraquinone nucleus.

3. Oxidation of a compound of formula VIII

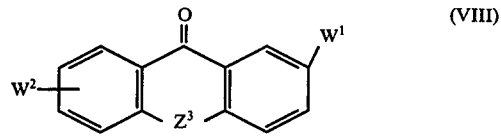
(VIII)

wherein one of $W^1$ and $W^2$ is a lower alkyl group or a group C(:O)R wherein R is an optionally substituted lower alkyl group having 1 to 4 carbon atoms, or is OH, and the other of $W^1$ and $W^2$ is $Z^1$ or $Z^2$, as appropriate, as defined in formula I; and $Z^3$ is as defined in formula I. Oxidation of compounds wherein $W^1$ and/or $W^2$ are lower alkyl groups may be effected with such conventional oxidising agents as acid or alkaline aqueous potassium permanganate solution; chromium trioxide, for example, with acetic acid or sulphuric acid; oxygen in the presence of a conventional catalyst such as lead, cobalt and manganese salts, for example, lead acetate; or aqueous solutions of sodium dichromate.

Oxidation of compounds wherein $W^1$ or $W^2$ are the groups C(:O)R may be effected with such conventional oxidising agents as chromium trioxide, for example, with acetic acid or sulphuric acid; aqueous solutions of salts of hypochlorous and hypobromous acids in the presence of a base; sodium or potassium dichromate with acetic acid; or nitric acid. These oxidation procedures are advantageously effected with heating in the liquid phase.

4. Oxidation of a compound of formula IX

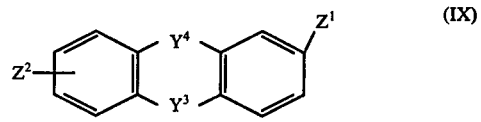
(IX)

wherein $Z^1$ and $Z^2$ have the meaning defined hereinbefore in formula I, $Y^3$ is a group $Z^3$ as defined hereinbefore in formula I and $Y^4$ is a methylene group; or $Y^4$ and $Y^3$ are the same or different and are each selected from CH and CR wherein R is lower alkyl. Oxidation of compounds of formula IX may be effected with such conventional oxidising agents as nitric acid; aqueous solutions of hypochlorous and hypobromous acids in the presence of base; chromium trioxide, for example with acetic acid or with sulphuric acid; or aqueous solutions of sodium dichromate.

Oxidation of compounds of formula IX wherein $Y^4$ is a methylene group and $Y^3$ is a bond, or $Y^4$ and $Y^3$ are each CH, may also be effected with such conventional oxidising agents as oxygen in the presence of triton B in pyridine solution; or oxygen in the presence of potassium t-butoxide in the presence of t-butanol and dimethylsulphoxide.

Compounds analogous to the compounds of formula IX wherein either of $Z^1$ and $Z^2$ is replaced by a group $W^1$ or $W^2$, as appropriate, as defined in formula VIII, may also be oxidised so as to produce carboxylic acids or salts of formula I. Oxidation in the case of such compounds may be effected with such conventional oxidising agents as chromium trioxide, for example, with acetic acid or with sulphuric acid,; or aqueous solutions of sodium dichromate. In the case of such compounds wherein neither of $W^1$ and $W^2$ is alkyl, oxidation may also be effected with such conventional oxidising agents as aqueous solutions of salts of hypobromous or hypochlorous acids in the presence of a base; or nitric acid. Advantageously any of the hereinbefore described oxidation procedures wherein aqueous solutions of sodium dichromate are employed, are carried out at an elevated temperature in a sealed container. Oxidation of the groups $W^1$ and $W^2$ in such a case is preferably, effected at a temperature of from 200° to 210° C. Oxidation of the tricyclic anthraceene; 9,10-dialkyl anthracene or anthrone nucleus in such a case is desirably effected at a temperature of from 250° to 260° C.

The compounds of formula I may also be prepared by formation of a 5-tetrazolyl group as the final step. Thus in formula I wherein one or both of $Z^1$ and $Z^2$ are tetrazolyl or (1-alkyl)tetrazolyl groups, these compounds may be prepared by reaction of hydrazoic acid or a salt thereof or nitrous acid with an appropriate compound of formula XIV wherein

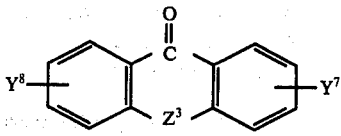
(XIV)

$Y^7$ is a group $Z^1$ as defined in formula I or a tetrazolyl group precursor and $Y^8$ is a group $Z^2$ as defined in formula (I) or a tetrazolyl group precursor, provided that at least one of $Y^7$ and $Y^8$ is a tetrazolyl group precursor.

When hydrazoic acid or a salt thereof is used, a suitable tetrazolyl group precursor is a group

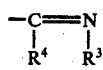

wherein $R^3$ and $R^4$ together form a bond (nitrile), $R^3$ is hydrogen or alkyl and $R^4$ is alkoxy having 1 to 6 carbon atoms (imidoester), thioalkyl having 1 to 6 carbon atoms (imidothioester), —NH—NH$_2$ (amidrazone), or amino (amidine) or $R^3$ is hydroxy and $R^4$ is amino (amidoxime), or $R^3$ is alkyl and $R^4$ is halogen (imidohalide). In the case of amidoximes and nitriles, only tetrazolyl compounds may be produced and in the case of imidohalides only akyltetrazolyl compounds may be produced. The reaction is preferably carried out in a polar aprotic liquid medium using a salt of hydrazoic acid.

When nitrous acid is used, a suitable tetrazolyl precursor group is a group

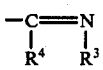

wherein $R^3$ is hydrogen or alkyl and $R^4$ is —NH—NH (amidrazone) or $R^3$ is hydrogen and $R^4$ is amino (amidine). In the latter case, reduction of the intermediate nitrosation product, with or without prior isolation, using for example sodium amalgam, is required to give the corresponding tetrazolyl compound.

The tetrazolyl compounds of formula-I thus prepared may be isolated as the free acid or as a tetrazolyl salt, and the one converted to the other in known manner and as specifically described below in relation to the carboxylic acids of formula I and their salts.

The 5-(1- and 2- alkyl)tetrazolyl compounds of formula I may be made from the corresponding tetrazolyl compounds of formula I or their salts by alkylation.

Salts of formula I may be isolated from a reaction medium by any conventional process for the isolation of salts from a solution thereof in a polar medium.

Desirably the salts of formula I are purified prior to incorporation in a pharmaceutical composition by any conventional method.

Esters and amides of acids of formula I may be prepared by any conventional method including esterification of the acid or acid chloride with an alkyl or aryl alcohol to yield the corresponding alkyl or aryl ester respectively and reaction of the acid or acid chloride with ammonia or an amine to yield the corresponding amide or substituted amide respectively. Compounds of formula I where $Z^1$ and $Z^2$ are different and are chosen from acid, ester, amide and salt functions, may be prepared by the above methods, and by partial hydrolysis, where appropriate.

The compounds of formula I are useful in the treatment or prophylaxis of mammalian allergic conditions such as asthma and other allergic chest conditions, hay fever (allergic rhinitis), conjunctivitis, urticaria and eczema. In particular they are of value in reaginic mediated Type I hypersensitivity asthma ('extrinsic asthma]) and the so-called 'intrinsic asthma' in which no sensitivity to extrinsic antigen can be shown.

The magnitude of a prophylactic or therapeutic dose of compound of formula I will of course vary with the nature of the severity of the allergic condition to be treated and with the particular compound of formula I and its route of administration. In general the dose range lies within the range of 2 μg. to 100 mg. per Kg. body weight of a mammal.

In the case of an allergic condition as defined hereinbefore, for example, allergic asthma, a suitable dosage is from 20 μg. to 0.5 mg., for example about 0.1 to 0.5 mg., of a compound of formula I, per Kg. of bodyweight of the patient undergoing treatment, when pulmonary administration as described hereinafter is employed. In the case where a composition for intravenous administration is employed a suitable dosage range is from 0.2 to 10 mg. (preferably 1 to 5 mg.) of a compound of formula I per Kg. of bodyweight of patient, and in the case where an oral composition is employed a suitable dosage range is from 1 to 50 mg. of a compound of formula I per Kg. of bodyweight of a patient, preferably from 10 to 40 mg/Kg.

In the case where a composition for nasal and ocular administration is employed, for example, in the treatment of allergic rhinitis, a suitable dose is from 0.5 to 25 mg. of a compound of formula I per patient.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients.

Desirably, each discrete unit contains from 50 mg. to 500 mg. of the active ingredient.

A valuable form of a pharmaceutical composition of the present invention, for use in the treatment of allergic asthma, is one suitable for pulmonary administration via the buccal cavity. Preferably the composition is such that particles having a diameter of 0.5 to 7μ, most preferably 1 to 6μ, containing active ingredient, are delivered into lungs of a patient. Such compositions are conveniently in the form of dry powders for administration from a powder inhalation device or self-propelling powder-dispensing containers; preferably the powders comprise particles containing active ingredient of which particles at least 98% by weight have a diameter greater than 0.5µ and at least 95% by number have a diameter less than 7µ. Most desirably at least 95% by weight of the particles have a diameter greater than 1µ and at least 90% by number of the particles have a diameter less than 6µ.

The compositions in the form of dry powders preferably include a solid fine powder diluent and are conveniently presented in a pierceable capsule, for example of gelatin.

Self-propelling compositions of the invention may be either powder-dispensing compositions or compositions dispensing the active ingredient in the form of droplets of a solution of suspension. Self-propelling powder-dispensing compositions include a liquid propellant having a boiling point at below 65° F at atmospheric pressure. Generally the propellant may constitute 50 to 9.9% w/w of the composition whilst the active ingredient may constitute 0.1 to 20% w/w, for example, about 2% w/w, of the composition. The carrier in such compositions may include other constituents, in particular a liquid non-ionic or solid anionic surfactant, or a solid diluent (preferably having a particle size of the same order as of the particles of active ingredient) or both. The surfactant may constitute up to 20% w/w, though preferably it constitutes below 1% w/w of the composition.

Self-propelling composition wherein the active ingredient is present in solution comprise an active ingredient, propellant and co-solvent, and advantageously an antioxidant stabiliser. The co-solvents may constitute 5 to 40% w/w of the composition, though preferably less than 20% w/w of the composition.

Compositions of the present invention may also be in the form of aqueous or dilute alcoholic solution, optionally a sterile solution, of the active ingredient for use in a nebuliser of atomiser.

Compositions of the present invention suitable for parenteral administration conveniently comprise sterile aqueous solutions of the active ingredient, which solutions are preferably isotonic with blood of a patient under treatment.

Pharmaceutical composition of the present invention suitable for topical use include compositions suitable for administration to the skin, eyes, nose and mouth. Compositions for use on the skin include lotions and creams comprising liquid or semi-solid emulsions, either oil-in-water or water-in-oil, and ointment, preferably containing from 0.2 to 5% w/v of the active ingredient. Desirably the creams and ointments should contain a preservative such as methyl hydroxybenzoate.

Compositions for administration to the eye include eye drops comprising the active ingredient in aqueous or oily solution and ointments, preferably containing 0.2 to 5% w/v of the active ingredient. The eye drops are desirably fungistatic and bacteriostatic and are preferably prepared sterile.

Compositions suitable for administration to the nose include powder, self-propelling and spray compositions similar to those already described under compositions suitable for pulmonary administration but having when dispersed, a somewhat larger particle size of the order of 10 to 200 microns. Other compositions suitable for nasal administration include a coarse powder having a particle size of 20 to 500 microns which is administered in the manner in which snuff is taken i.e. by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100 mg. of the active ingredient in a flavoured base, usually sucrose and acacia or tragacanth; and pastilles comprising 10 to 100 mg. of the active ingredient in an inert base such as gelatin and glycerin; or sucrose and acacia.

Other therapeutic ingredients suitable for inclusion in the hereinbefore described compositions, especially in the case of those compositions intended for use in the treatment of allergic asthma, include bronchodilators such as isoprenaline, adrenaline, orciprenaline, isoethanine and physiologically acceptable acid addition salts thereof, especially isoprenaline sulphate. Conveniently the bronchodilator is present in an amount of 0.1 to 50% w/w of the weight of active ingredient present.

Included within the scope of the present invention, but in no way limited thereto, are the following specific features:

1. A compound of formula I as defined hereinabove, where novel.
2. The synthesis of compounds of formula I as defined hereinabove, by any method known in the art for preparing them and compounds of analogous chemical structure.
3. Pharmaceutical compositions comprising a compound of formula I as defined hereinabove in association with a pharmaceutically acceptable carrier therefor.
4. The preparation of pharmaceutical composition comprising a compound of formula I as defined hereinabove as an active ingredient, by any conventional method, including admixture of the ingredients.
5. A method of treatment or prophylaxis of mammalian allergic conditions comprising administration of a therapeutic or prophylactic dose respectively, of a compound of formula I as defined hereinabove.

Set forth below are examples of this invention.

EXAMPLE 1

2,6-Di-(5-tetrazolyl)anthraquinone (a) Anthraquinone-2,6-dicarboxamide

Anthraquinone-2,6-dicarboxylic acid (5.0g.) was boiled with thionyl chloride (50 ml.) and dimethylformamide (0.25 ml.) for 45 min. The resulting clear solution was evaporated to dryness and the residual acid chloride treated with 0.880 ammonia. After standing for 30 min, the crude amide was filtered off, washed with water and dried, m.pt. 420° (decomp.).

(b) 2,6-Dicyanoanthraquinone

Thionyl chloride (10.0 ml) was added to dimethylformamide (100 ml.) at −30° C. with stirring in 1 ml. portions. To the resulting solution, anthraquinone-2,6-dicarboxamide (4.74g.) was added in one portion and the temperature of the mixture was allowed to rise slowly to 5° C. by placing in an ice-bath. After 30 min. at this temperature, the mixture was heated over 30 min.

to 65° C. The heterogeneous mixture was then poured into iced water and the solid filtered off, dried, and recrystallised from dimethylsulphoxide, 2.60g. m.p. 392° C. (decomp.) in a sealed, evacuated tube.

(c) 2,6-Di-(5-tetrazolyl)anthraquinone 2,6-Dicyanoanthraquinone (2.06g.), sodium azide (1.30g.), ammonium chloride (1.07g.) and dimethylformamide (100 ml.) were stirred together at 105°-110° C. for 24 hr. The mixture was poured into an excess of dilute hydrochloric acid, and the solid product filtered off and washed with water. The solid was treated with 2½% potassium bicarbonate solution (100 ml.) and some in-insoluble material was filtered off. The filtrate was acidified with dilute hydrochloric acid, heated to boiling to coagulate the gelatinous precipitate, and the crude product filtered off, dried, and recrystallised from dimethylformamide decomposes at about 300° C.

EXAMPLE 2

5-(7-Propoxycarbonyl-2-fluorenone)tetrazole (a) Dipropyl fluorenone-2,7-dicarboxylate (m.p. 146.5° to 148° C.) was prepared from fluorenone-2,7-dicarboxylic acid by esterification with propanol in the presence of sulphuric acid. This diester was hydrolysed to the 7-propoxycarbonylfluorenone-2-carboxylic acid (m.p. 250°-252° C.) using sodium hydroxide in the presence of propanol. This half-ester was treated with thionyl chloride to provide the corresponding acid chloride, and the latter converted to the corresponding amide (m.p. 278°-279° C) by treatment with aqueous ammonia.

(b) 7-Propoxycarbonylfluorenone-2-carboxamide (3.8g.) was dissolved in dimethylformamide (50 ml.) with warming and the solution was then stirred and cooled to −25° C. Thionyl chloride (7.55 ml) was added dropwise over 10 minutes and the mixture was allowed to warm to 0° C., left at this temperature for 60 hours, and then treated with an ice water mixture. The pale yellow solid was filtered, washed with water and dried in vacuo to give 7-propoxycarbonylfluorenone-2-carbonitrile, m. pt. 198°-199° C.

(c) A portion (2g.) of this nitrile, sodium azide (450 mg.) and ammonium chloride (400 mg.) in dimethylformamide (20 ml.) were heated to 100° C., with stirring, for 18 hours. The mixture was cooled, poured into water (200 ml.) and made just acid with 2N hydrochloric acid. The gelatinous precipitate was filtered, washed with water, and redissolved in aqueous sodium bicarbonate; the solution was filtered and then acidified with 2N hydrochloric acid. The resulting solid was filtered, dissolved in 2N aqueous ammonia, reprecipitated with hydrochloric acid and then filtered, washed with water and dried in vacuo to give 5-(7-propoxycarbonyl-2-fluorenone)tetrazole, m.pt. 227°-228° C. (decomp.)

EXAMPLE 3

Preparation of 2,7-Di(5-tetrazolyl)fluorenone

A. Preparation of 2,7-Dicyanofluorenone

A mixture of 2,7-dibromofluorenone (14.92 g) and cuprous cyanide (9.35 g) in dimethylformamide (40 ml) was heated to reflux for 5 hours. The hot mixture was added to a solution of ferric chloride (38 g) in water (57 ml) and concentrated hydrochloric acid (9.5 ml). The mixture was heated on a steam bath for 2 hours, filtered, treated again with a similar aqueous acidic solution of ferric chloride and then filtered, washed well with water and dried in vacuo to give 2,7-dicyanofluorenone as a yellow solid m.p. above 300° C.

B. Preparation of 2,7-Di(5-tetrazolyl)fluorenone

A mixture of 2,7-dicyanofluorenone (4.6 g) sodium azide (2.62 g) and ammonium chloride (2.6 g) in dimethylformamide (25 ml) was stirred and heated to 100° C for 10 hours. The mixture was cooled, treated with an excess of 2N hydrochloric acid and the solid was filtered, washed with water, dried in vacuo and recrystallised from a mixture of dimethylformamide and water. This product was dissolved in an excess of 0.1N aqueous sodium hydroxide, the solution was filtered and acidified with hydrochloric acid. The resulting precipitate was filtered, washed with water and dried in vacuo to give 2,7-di-(5-tetrazolyl)fluorenone, m.p. above 300° C.

EXAMPLE 4

5-(7-Butylfluorenone-2)-tetrazole

A mixture of 7-butylfluorenone-2-carboxylic acid (800 mg), thionyl chloride (5 ml) and dimethylformamide (2 drops) was heated to reflux for 2 hours and then evaporated under reduced pressure. The residue was cooled to 0° C. and treated with .880 aqueous ammonia; the resulting mixture was stirred at room temperature for one hour, then at 100° C. for 15 minutes, and was then cooled and filtered to give 7-butylfluorenone-2-carboxamide, m.p. 185°-190° C.

The above amide (650 mg) was dissolved in dimethylformamide (11 ml) and the solution was cooled to −20° C, stirred, and treated dropwise with thionyl chloride (1.5 ml). After stirring for a further 30 minutes at −20° C. the solution was allowed to attain room temperature over 1 hour and was then poured into ice-water (50 ml). The resulting amorphous product was extracted into chloroform and the chloroform solution was washed well with water, dried over anhydrous sodium sulphate and evaporated. The residual amorphous nitrile was dissolved in dimethylformamide (10 ml), treated with sodium azide (200 mg) and ammonium chloride (180 mg) and heated to 110° C, with stirring, for 20 hours. The mixture was poured into water (50 ml), acidified with hydrochloric acid, and the solid was filtered, washed with water and dried. Recrystallisation from ethanol gave pure 5-(7-butylfluorenone-2)-tetrazole, m.p. 233°-234° C. (decomp.).

EXAMPLE 5

5-(7-Bromofluorenone-2)-tetrazole

A mixture of 7-bromofluorenone-2-carboxylic acid (850 mg), thionyl chloride (5 ml) and dimethylformamide (2 drops) was heated to reflux for 4 hours and then evaporated under reduced pressure. The residue was cooled to 0° C. and treated with aqueous ammonia; the mixture was stirred at room temperature for 16 hours and at 100° C for 30 minutes and was then cooled and filtered to give 7-bromofluorenone-2-carboxamide, m.p. 270°-274° C.

This amide (700 mg) was dissolved in hot dimethylformamide (11 ml) and the solution was cooled to −20° C, stirred, and treated dropwise with thionyl chloride (1.5 ml); a yellow solid began to separate during the addition. The mixture was stirred for a further hour at −20° C, then for 3 hours at room temperature, and then poured onto ice-water (50 ml). The yellow solid was filtered, washed well with water and dried to give 7- bromofluorenone-2-carbonitrile, m.p. 205°–210° C. This nitrile (500 mg) in dimethylformamide (10 ml) was treated with sodium azide (200 mg) and ammonium chloride (180 mg) and the mixture was stirred and heated to 110° C. for 20 hours. The mixture was then poured into water (50 ml), acidified with hydrochloric acid, and the yellow solid was filtered, washed with water and dried to give 5-(7-bromofluorenone-2)-tetrazole, m.p. 290°–295° C. (decomp.).

| Example A - Powder Capsules for Inhalation | |
|---|---|
| 2,7-Di-(5-tetrazolyl)fluorenone (0.5 – 7.0 μm powder) | 4mg |
| Lactose (30 – 90 μm powder) | 46.0mg |

The powders were mixed until homogeneous and filled into suitably sized hard gelatin capsules, 50mg of mixture per capsule.

| Example B - Inhalation Aerosol | | |
|---|---|---|
| 2,7-Di-(5-tetrazolyl)fluorenone (0.5 – 7.0 μm powder) | | 200mg |
| Sorbitan Trioleate | | 100mg |
| Saccharin Sodium (0.5 – 7.0 μm powder) | | 5mg |
| Menthol | | 2mg |
| Trichlorofluoromethane | | 4.5 g |
| Dichlorodifluoromethane | to | 10.0ml |

The Sorbitan Trioleate and Menthol were dissolved in the Trichlorofluoromethane. The Saccharin Sodium and diacid were dispersed in the mixture which was then transferred to a suitable aerosol canister and the Dichlorofluoromethane injected through the valve system. This composition provides 2mg of Acid in each 100μl. dose.

What we claim is:

1. A method of inhibiting the symptoms of asthma or allergic rhinitis in a mammal susceptible to asthma or allergic rhinitis which comprises the administration to said mammal of a prophylactically effective, non-toxic amount of a compound of formula (I)

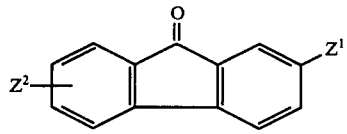

wherein one of $Z^1$ and $Z^2$ is a 5-(1-R)tetrazolyl or a 5-(2-R) tetrazolyl group in which R is hydrogen or alkyl having 1 to 6 carbon atoms, and the other is selected from the group consisting of carboxy, 5-(1-R) tetrazolyl and 5-(2-R)tetrazolyl as defined, provided that when $Z^2$ is 5-(1-R)tetrazolyl or 5-(2-R)tetrazolyl then $Z^1$ is carboxy; and $Z^2$ is also selected from the group consisting of hydrogen, nitro, cyano, halogen, alkylsulphinyl and alkylsulphonyl, acyl, alkyl, or alkoxy wherein the "alkyl" moiety of each of the acyl, alkyl, alkoxy, alkylsulphinyl and alkylsulphonyl groups has 1 to 6 carbon atoms; together with salts, and, when $Z^1$ or $Z^2$ is carboxy, alkyl esters having 1 to 6 carbons and unsubstituted amides or amides substituted by one or two alkyl groups having 1 to 6 carbons of said compounds of formula (I).

2. The method of claim 1 wherein in formula (I) one of $Z^1$ and $Z^2$ is a 5-(1-R) tetrazolyl or a 5-(2-R)tetrazolyl group wherein R is hydrogen or alkyl having 1 to 6 carbon atoms, and the other is selected from the group consisting of carboxy, 5-(1-R)tetrazolyl and 5-(2-R)tetrazolyl as defined; and $Z^2$ is also selected from hydrogen, nitro, cyano, chlorine, bromine, acyl, alkyl or alkoxy wherein the "alkyl" moiety of each of the acyl, alkyl and alkoxy groups has 1 to 6 carbon atoms; together with salts, and when $Z^1$ or $Z^2$ is carboxy, esters and amides thereof as defined in claim 1.

3. The method of claim 1 wherein in formula (I) one of $Z^1$ and $Z^2$ is 5-tetrazolyl and the other is carboxy, together with salts of said compounds.

4. The method of claim 1 wherein in formula (I) $Z^2$ is hydrogen or is a substituent as defined therein in the 7-position.

5. The method of claim 1 wherein in formula (I) one of $Z^1$ and $Z^2$ is 5-tetrazolyl and the other is carboxy or 5-tetrazolyl together with salts of said compounds.

6. The method of claim 4 wherein in formula (I) $Z^2$ is in the 7-position.

7. The method of claim 6 wherein $Z^2$ is propoxycarbonyl, butyl or bromine.

8. The method of claim 1 wherein the tricyclic compound is selected from:
5-(7-propoxycarbonyl-2-fluorenone)tetrazole;
5-(7-butyl-2-fluorenone)tetrazole;
5-(7-bromo-2-fluorenone)tetrazole;
and pharmaceutically acceptable salts thereof.

9. The method of claim 1 wherein the prophylactically effective dose is from 2 μg to 100 mg. per kilogram bodyweight of the mammal.

10. The method of claim 1 comprising administration into the lung of the mammal of a dose of 20 μg to 0.5 mg of said compound for the treatment or prophylaxis of allergic asthma.

11. The method of claim 1 wherein administration is effected by the oral route.

12. The method of claim 1 wherein the anti-allergic dose is from 1 to 50 mg of said compound of said compound of formula (I) per kilogram bodyweight of the mammal.

13. The method of claim 1 wherein said condition is allergic asthma.

14. The method of inhibiting the symptoms of conjunctivities in a mammal having conjunctivitis which comprises administration to said mammal of a prophylactically effective non-toxic amount of a compound of formula I as defined in claim 1.

15. The method of inhibiting the symptoms of urticaria in a mammal having urticaria which comprises administration to said mammal of a prophylactically effective non-toxic amount of a compound of formula I as defined in claim 1.

16. The method of inhibiting the symptoms of eczema in a mammal having eczema which comprises administration to said mammal of a prophylactically effective non-toxic amount of a compound of formula I as defined in claim 1.

17. A pharmaceutical composition suitable for administration to a mammal to inhibit the symptoms of asthma or allergic rhinitis which comprises a prophylactically effective non-toxic amount of a compound of formula (I)

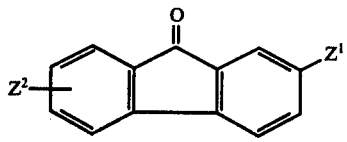 (I)

wherein one of $Z^1$ and $Z^2$ is a 5-(1-R)tetrazolyl or a 5-(2-R) tetrazolyl group in which R is hydrogen or alkyl having 1 to 6 carbon atoms, and the other is selected from the group consisting of carboxy, 5-I1-R)tetrazolyl and 5-(2-R)tetrazolyl as defined, provided that when $Z^2$ is 5-(1-R)tetrazolyl or 5-(2-R)tetrazolyl then $Z^1$ is carboxy and $Z^2$ is also selected from the group consisting of hydrogen, nitro, cyano, halogen, alkylsulphinyl, alkylsulphonyl, acyl, alkyl or alkoxy wherein the "alkyl" moiety of each of the acyl, alkyl, alkoxy, alkylsulphinyl, and alkylsulphonyl groups has 1 to 6 carbon atoms; together with salts and when $Z^1$ or $Z^2$ is carboxy, alkyl esters having 1 to 6 carbons and unsubstituted amides or amides substituted by one or two alkyl groups having 1 to 6 carbons of said compounds of formula (I) in association with a pharmaceutically acceptable carrier therefor.

18. The composition as claimed in claim 17 wherein in formula (I) one of $Z^1$ and $Z^2$ is a 5-(1-R)tetrazolyl or a 5-(2-R)tetrazolyl group wherein R is hydrogen or alkyl having 1 to 6 carbon atoms, and the other is selected from the group consisting of carboxy, 5-(1-R)tetrazolyl and 5-(2-R)tetrazolyl as defined; and $Z^2$ is also selected from hydrogen, nitro, cyano, chlorine, bromine, acyl, alkyl or alkoxy wherein the "alkyl" moiety of each of the acyl, alkyl and alkoxy groups has 1 to 6 carbon atoms; together with salts, and when $Z^1$ or $Z^2$ is carboxy, esters and amides thereof as defined in claim 17.

19. The composition of claim 17 wherein in formula (I) one of $Z^1$ and $Z^2$ is 5-tetrazolyl and the other is carboxy, together with salts of said compounds.

20. The composition of claim 17 wherein in formula (I) $Z^2$ is hydrogen or is a substituent as defined therein in the 7-position.

21. The composition of claim 20 wherein in formula (I) one of $Z^1$ and $Z^2$ is 5-tetrazolyl and the other is carboxy together with salts of said compounds.

22. The composition of claim 17 wherein in formula (I) $Z^2$ is in the 7-position.

23. The composition of claim 17 comprising a compound selected from;
5-(7-propoxycarbonyl-2-fluorenone)tetrazole;
5-(7-butyl-2-fluorenone)tetrazole;
5-(7-bromo-2-fluorenone)tetrazole;
and pharmaceutically acceptable salts thereof.

24. The composition of claim 17 wherein the pharmaceutically acceptable salt is selected from a sodium, potassium, magnesium, calcium or ammonium salt and a salt with an organic base.

25. The composition of claim 17 wherein the composition is in the form of a discrete dosage unit selected from a tablet, capsule, lozenge and sachet, each unit containing from 50 to 500 mg. of said tricyclic compound.

26. The composition of claim 18 wherein said tricyclic compound is in the form of a powder adapted for pulmonary administration.

27. The composition of claim 26 in the form of a self propelling aerosol composition comprising said tricyclic compound dispersed in a liquid propellant in a sealed valved container.

28. The composition of claim 26 wherein said powder is incorporated in a capsule suitable for use in an inhalation device.

29. The composition of claim 22 wherein $Z^2$ is selected from butyl, bromine and propoxycarbonyl.

30. The composition suitable for administration to a mammal to inhibit the symptoms of conjunctivitis urticaria or eczema which comprises a prophylactically effective non-toxic amount of a compund of formula (I) as defined in claim 1.

* * * * *